US00PP36525P2

(12) United States Plant Patent
van Zoest

(10) Patent No.: US PP36,525 P2
(45) Date of Patent: Mar. 4, 2025

(54) ***CLEMATIS* PLANT NAMED 'Zo23015'**

(50) Latin Name: ***Clematis* hybrid**
Varietal Denomination: Zo23015

(71) Applicant: Jos van Zoest, Boskoop (NL)

(72) Inventor: Jos van Zoest, Boskoop (NL)

(73) Assignee: J. VAN ZOEST BEHEER B.V., Boskoop (NL)

( * ) Notice: Subject to any disclaimer, the term of this patent is extended or adjusted under 35 U.S.C. 154(b) by 0 days.

(21) Appl. No.: 18/808,076

(22) Filed: Aug. 19, 2024

(30) Foreign Application Priority Data

Jul. 27, 2024 (QZ) ..... PBR 20241767

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
CPC ..... A01H 5/02; A01H 5/00; A01H 6/72
See application file for complete search history.

(56) References Cited

PUBLICATIONS

CPVO Application Consultation Version 4.21.4 retrieved on Nov. 20, 2024 at https://online.plantvarieties.eu/publicConsultationDetails?registerId=20241767&denomination=zo23015, 2 pp. (Year: 2024).*

* cited by examiner

*Primary Examiner* — June Hwu
(74) *Attorney, Agent, or Firm* — Penny J. Aguirre

(57) ABSTRACT

A new cultivar of *Clematis* plant named 'Zo23015' that is characterized by its flowers with dainty, narrow tepals that are deep red in color, its large flowers, its flowers that are single, and its flowers with yellow-green stamens.

3 Drawing Sheets

Botanical classification: *Clematis* hybrid.
Variety denomination: 'Zo23015'.

CROSS REFERENCE TO RELATED APPLICATIONS

This application claims priority to European Community Plant Variety Office (CPVO) Plant Breeder's Rights Application No. 2024/1767 filed on Jul. 27, 2024, the entire contents of which is incorporated by reference herein. The information for the plant breeders' rights application was received directly from the Inventor.

BACKGROUND OF THE INVENTION

The present invention relates to a new and distinct cultivar of *Clematis* plant of hybrid origin and will be referred to hereafter by its cultivar name 'Zo23015'. 'Zo23015' is an herbaceous perennial vine grown for use as a landscape plant.

'Zo23015' arose from an on-going breeding program conducted by the Inventor in Boskoop, The Netherlands. The goal was to develop a new cultivar of Viticella type *Clematis* with large flowers that are deep red in color. The new cultivar arose from a cross made in 2017 between a proprietary seedling from the Inventors breeding program, ref no. 20090087, as the female parent and 'Niobe' (not patented) as the male parent. The Inventor selected 'Zo23015' as a single unique plant amongst the seedlings that resulted from the above cross in August of 2019.

Asexual propagation of the new cultivar was first accomplished by softwood stem cuttings under the direction of the Inventor in August of 2019 in Boskoop, The Netherlands.

Asexual propagation by softwood stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish *Clematis* 'Zo23015' as a unique cultivar of *Clematis*.

1. 'Zo23015' exhibits flowers with dainty, narrow tepals that are deep red in color.
2. 'Zo23015' exhibits large flowers.
3. 'Zo23015' exhibits flowers that are single.
4. 'Zo23015' exhibits flowers with yellow-green stamens.

The female parent of 'Zo23015' differs from 'Zo23015' in having flowers that are smaller in size, light purple-red in color. The male parent of 'Zo23015' differs from 'Zo23015' in having flowers that are larger in size with tepals that are broader and in being more susceptible to *Clematis* wilt. 'Zo23015' can be most closely compared to the *Clematis* cultivars 'Madame Julia Correvon' (not patented) and 'Rubra' (not patented). Both are similar to 'Zo23015' in having flowers with red tepals. 'Madame Julia Correvon' differs from 'Zo23015' in having a flowers that are slightly smaller in size with tepals that are broader and slightly lighter red in color. 'Rubra' differs from 'Zo23015' in having flowers that are larger in size with tepals that are broader and stamens that are blackish in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantarium/groen-direkt, Crocus, Esveld Shop, RHS Plants, Waitrose Garden, Vitiflora, Plantes-web, Goerdemorgen Chrysant, KVBC, Promesse de fleurs, Clematite, De Bloeimeesters, FloraXchange, Truffaut, FlorAccess, FloraNews, Dobies, HortWeek, Van Meuwen, Thompson & Morgan, Suttons Seeds, and Camolin Potting Shed.

BRIEF DESCRIPTION OF THE DRAWINGS

The accompanying color photographs illustrate the overall appearance and distinct characteristics of the new *Clematis*. The photographs were taken of a 15-month-old plant as grown outdoors in a 13-cm container and tied to a cane in Boskoop, The Netherlands.

The photograph in FIG. 1 provides a side view of 'Zo23015' in bloom.

Figure 1:
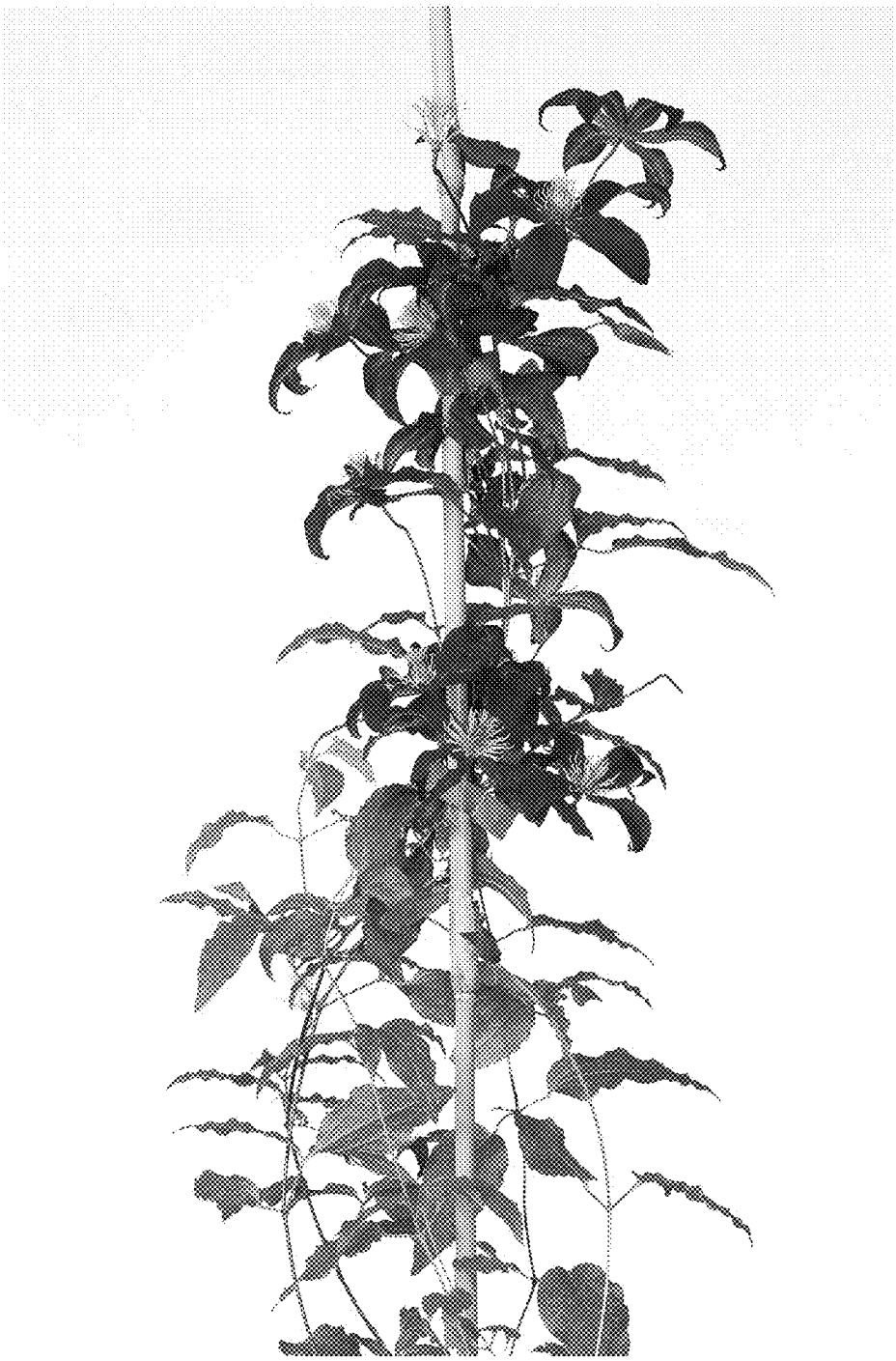
Figure 2:
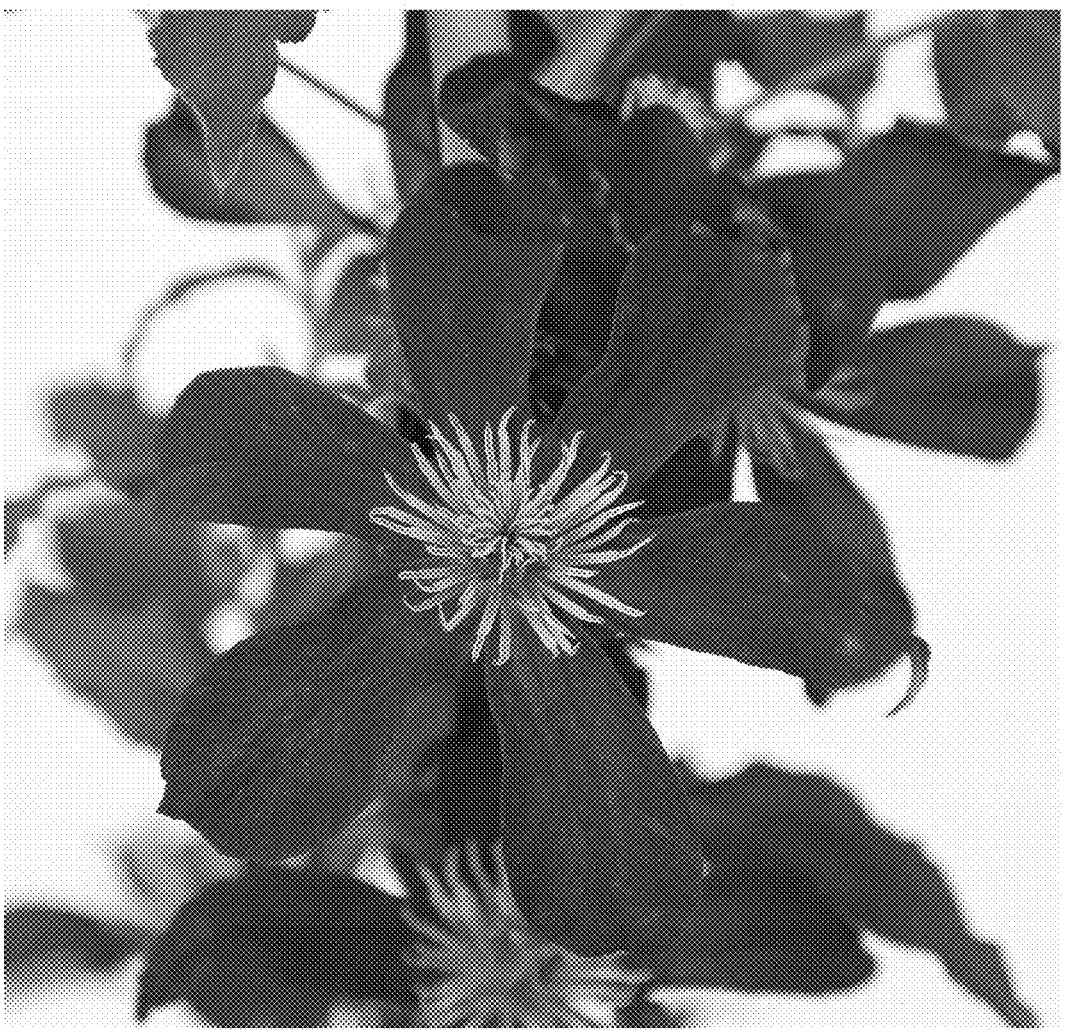

The photograph in FIG. 2 provides a close-up view of a flower of 'Zo23015'.

Figure 3:
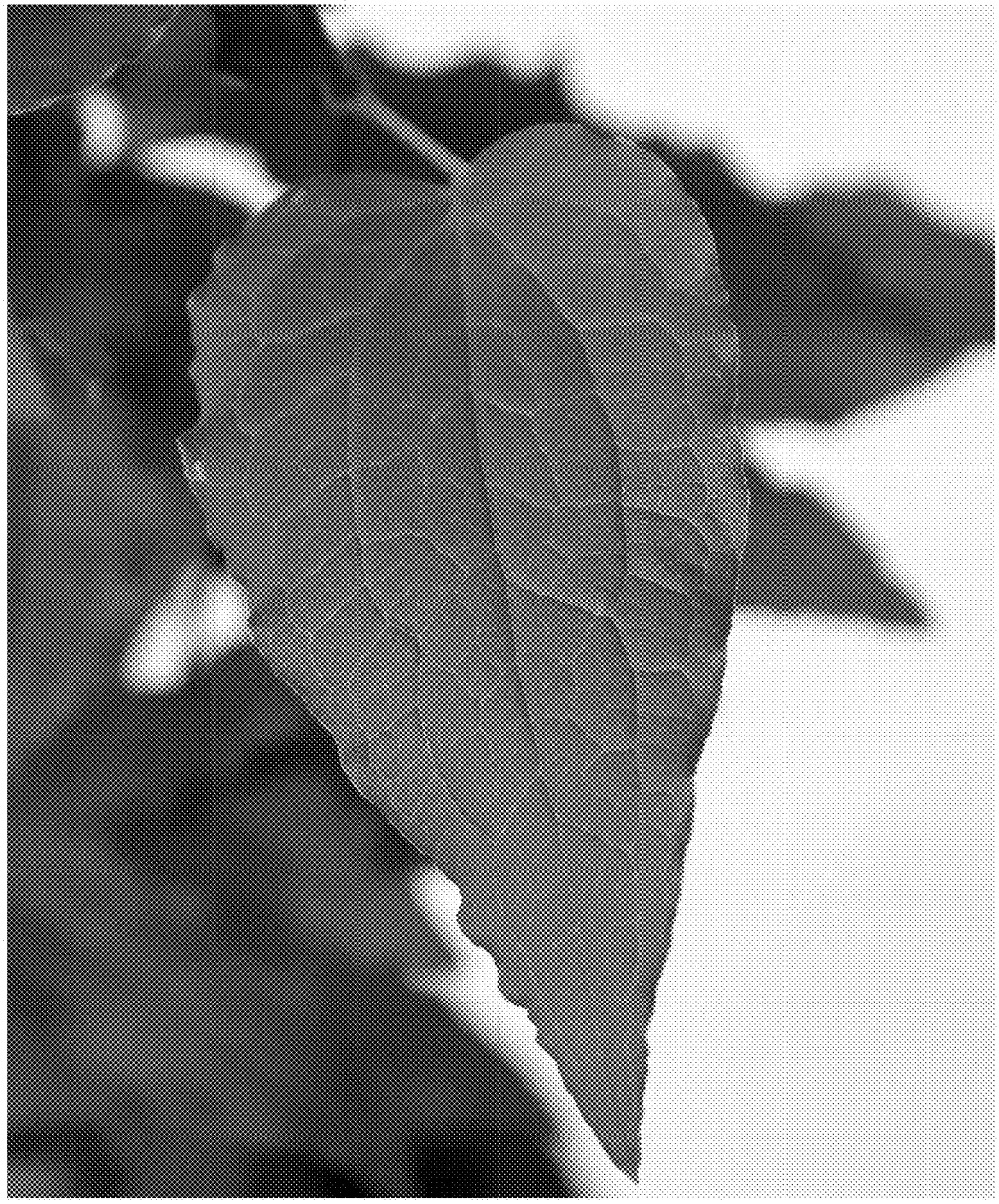

The photograph in FIG. 3 provides a close-up view of a single leaf of 'Zo23015'.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of 15-month-old plants as grown outdoors in 13-cm containers and tied to canes in Boskoop, The Netherlands. The phenotype of the new cultivar may vary with variations in environmental, climatic, and cultural conditions, as the cultivar has not been tested under all possible environmental conditions. The color determination is in accordance with The 2015 Colour Chart of The Royal Horticultural Society, London, England, except where general color terms of ordinary dictionary significance are used.

General description:

*Blooming period*.—June into September in The Netherlands.

*Plant type*.—Deciduous woody perennial, pruning group 3.

*Plant habit*.—Vine, (typically tied to trellis or cane) with blooms on main and lateral branches.

*Height and spread*.—Height; soil level to top of foliar plane 65.8 cm, soil level to top of floral plane 68.7 cm, diameter; 23.1 cm, as a 15-month old plant in a 13-cm container, up to 2.5 m in height when grown in the landscape.

*Hardiness*.—At least in U.S.D.A. Zones 6 to 10.

*Diseases and pests*.—No susceptibility or resistance to diseases or pests has been observed.

*Root description*.—Fleshy.

*Propagation*.—Softwood stem cuttings.

*Root development*.—An average of 6 to 8 weeks for root initiation and 5 months to produce a young rooted plant.

*Growth rate*.—Moderate.

Branch description:

*Branch shape*.—Angled.

*Branch color*.—Young; 144A, mature; 164A, internodes 164A, bark a blend of 165A and 200D.

*Branch size*.—Main branches; 56.9 cm in length, 2 mm in diameter, lateral branches; 3.8 cm in length, 1 mm in diameter.

*Branch surface*.—Young and mature branches; matt and moderately covered with short pubescence; up to 0.3 mm in length and too small to measure color, older wood; smooth barked.

*Branch strength*.—Strong but flexible, support needed.

*Branch angle*.—Average of 80°.

*Branching*.—Average of 4 primary branches, 6 lateral branches per main branch.

*Internode length*.—Main stems; average of 8.2 cm, lateral stems; average of 3.8 cm.

Foliage description:

*Leaf arrangement*.—Opposite.

*Leaf division*.—Compound (tri-foliate) and single, about 50% of each type.

*Leaf quantity per plant*.—Main branch; 14 (7 pairs), lateral branch; 2 (1 pair).

*Leaf shape*.—Compound leaves broadly ovate to deltoid in outline, single leaves narrow ovate to ovate.

*Leaf aspect*.—Flat to slightly carinate.

*Leaf base*.—Nearly obtuse to obtuse.

*Leaf apex*.—Narrowly acute.

*Leaf size*.—Compound; an average of 8.4 cm in length and 9.9 cm in width, single leaves on lateral branch; 7.5 cm in length, 3.7 cm in width.

*Leaflet quantity per compound leaf*.—3.

*Leaflet shape*.—Narrow ovate to ovate.

*Leaflet base*.—Nearly obtuse to obtuse.

*Leaflet apex*.—Narrowly acute.

*Leaf and Leaflet venation*.—Pinnate, upper surface; 146C, lower surface; 146B and 146C.

*Leaf and leaflet margins*.—Entire, slightly undulate, unlobed.

*Leaf and leaflet surface*.—Upper surface; glabrous, very slightly glossy, lower surface; glabrous, moderately glossy, margins moderately covered with soft pubescent hairs; 0.3 mm in length and too small to measure color, both surfaces non-rugose.

*Leaflet size*.—Terminal; an average of 6.7 cm in length and 2.6 cm in width, laterals; an average of 5.4 cm in length and 2 cm in width.

*Leaf and leaflet color*.—Young upper surface; 143A, young lower surface; 144A, mature upper surface; NN137A and NN137B, mature lower surface; 147B, no fall color.

*Petioles*.—Compound leaves an average of 2.9 cm in length and 1 mm in diameter, single leaves an average of 1.8 cm in length and 1 mm in diameter, strong, color; 144A, surface densely covered with short pubescent hairs; 0.3 mm in length, too small to measure color.

*Petiolules*.—An average of 3.5 mm in length and 1 mm in diameter on terminal leaflet and an average of 1 cm in length and 1 mm in diameter on lateral leaflets, strong, color; 144A, surface densely covered with short pubescent hairs; 0.3 mm in length, too small to measure color.

Inflorescence description:

*Inflorescence type*.—Solitary, single flowers.

*Inflorescence arrangement*.—Terminal on main stems and lateral stems.

*Peduncles*.—Average of 5.4 cm in length, 1 mm in diameter, strong, color 146B, surface moderately glossy and moderately covered with short pubescent hairs; 0.4 mm in length and about 156A in color.

*Pedicels*.—None observed.

*Flower buds*.—Upright to slightly outward, lanceolate in shape, 2.5 cm in length, 7 mm in diameter, color; 146C and tinged at the tip with N200A and N200B, surface is moderately covered with soft pubescent hairs; 0.5 mm in length, about 156A in color.

*Flower fragrance*.—None.

*Lastingness of the flowers*.—14 days, self-cleaning.

*Flower quantity*.—Freely flowering, average of 44 flowers and 4 flower buds per plant.

*Flower shape*.—Rotate.

*Flower aspect*.—Upright and slightly outward.

*Flower size*.—Average of 7.8 cm in diameter, 3.2 cm in depth.

*Tepal number*.—6, occasionally 5 or 4.

*Tepal shape*.—Elliptic, tip curved downward.

*Tepal aspect*.—Horizontal and curved downward.

*Tepal apex*.—Apiculate.

*Tepal base*.—Cuneate.

*Tepal margin*.—Entire, slightly coarsely undulate.

*Tepal surface*.—Upper surface; very slightly glossy, velvety, lower surface; very slightly glossy, densely covered with soft pubescent hairs; 0.5 mm in length, 156A in color.

*Tepal color*.—When opening upper surface; 187C, when opening lower surface; 183B, central band 146B, veins 165A, when fully open upper surface; a blend of 59B and 187D, central band a blend of 59A and 187D, when fully open lower surface; 186C, central band 146D, veins 178A.

*Tepal size*.—An average of 4.65 cm in length and 1.8 cm in width.

*Perianth*.—No separate petals, only tepals.

Reproductive organs:

*Gynoecium*.—Pistils; 30, 1.2 cm in length, stigma; pointed in shape, 0.7 mm in length, 0.3 mm in diameter, 148D in color, style; 5 mm in length, 148A in color, ovary; 146D in color.

*Androecium*.—Stamens; 35, filaments; 9 mm in length, 145C in color and tinged 75C to 75D at apex, anthers; 4 mm in length, 1 mm in width, basifixed, narrow oblong in shape, and 144A in color, pollen; none observed.

*Seed*.—No seed heads have been observed to date.

It is claimed:

1. A new and distinct cultivar of *Clematis* plant named 'Zo23015' as herein illustrated and described.

* * * * *